(12) United States Patent
Peters et al.

(10) Patent No.: US 7,514,450 B2
(45) Date of Patent: Apr. 7, 2009

(54) AZABICYCLIC ARYL DERIVATIVES

(75) Inventors: Dan Peters, Ballerup (DK); Gunnar M. Olsen, Ballerup (DK); Elsebet Østergaard Nielsen, Ballerup (DK); Tino Dyhring Jørgensen, Ballerup (DK); Daniel B. Timmermann, Ballerup (DK)

(73) Assignee: NeuroSearch A/S, Ballerup (DK)

( * ) Notice: Subject to any disclaimer, the term of this patent is extended or adjusted under 35 U.S.C. 154(b) by 231 days.

(21) Appl. No.: 10/591,871

(22) PCT Filed: May 10, 2005

(86) PCT No.: PCT/EP2005/052107

§ 371 (c)(1),
(2), (4) Date: Sep. 7, 2006

(87) PCT Pub. No.: WO2005/111033

PCT Pub. Date: Nov. 24, 2005

(65) Prior Publication Data

US 2007/0203117 A1    Aug. 30, 2007

(30) Foreign Application Priority Data

May 19, 2004   (DK) ................. 2004 00799

(51) Int. Cl.
*A01N 43/90* (2006.01)
*A61K 31/44* (2006.01)
*C07D 453/02* (2006.01)

(52) U.S. Cl. ........................ 514/305; 546/137
(58) Field of Classification Search ........... 546/112, 546/133, 137; 514/299, 305
See application file for complete search history.

(56) References Cited

U.S. PATENT DOCUMENTS

| 2002/0042428 A1 | 4/2002 | Myers et al. |
| 2002/0052389 A1 | 5/2002 | Myers et al. |

FOREIGN PATENT DOCUMENTS

| WO | WO-02/15662 A1 | 2/2002 |
| WO | WO-02/16355 A1 | 2/2002 |
| WO | WO-02/17358 A1 | 2/2002 |
| WO | WO-03/040147 A1 | 5/2003 |
| WO | WO-03/104227 A1 | 12/2003 |
| WO | WO-2004/076453 A1 | 9/2004 |

OTHER PUBLICATIONS

Moore et al., Drugs & Aging (1999), 15(1), pp. 15-28.*
Hinshaw et al., J. Med. Chem., 2003, vol. 46, pp. 4240-4243.*
Brown et al., Bioorganic & Medicinal Chemistry Letters, 2001, vol. 11, pp. 2213-2216.*
Brown et al., J. Med. Chem. 1999, vol. 42, pp. 1306-1311.*

* cited by examiner

*Primary Examiner*—D. Margaret Seaman
*Assistant Examiner*—Niloofar Rahmani
(74) *Attorney, Agent, or Firm*—Birch, Stewart, Kolasch & Birch, LLP

(57) ABSTRACT

This invention relates to novel azabicyclic aryl derivatives which are found to be cholinergic ligands at the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

4 Claims, No Drawings

AZABICYCLIC ARYL DERIVATIVES

TECHNICAL FIELD

This invention relates to novel azabicyclic aryl derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism.

WO 2002/15662, WO 2002/16355, WO 2002/17358 and WO 2003/040147 (Pharmacia & Upjohn) describe azabicyclo arylamides useful as nicotinic acetyicholine receptor agonists. However, the azabicyclic aryl derivatives of the present invention are not described.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), and in particular the nicotinic acetylcholine α7 receptor subtype, the serotonin receptor (5-HTR), the dopamine receptor (DAR) and the norepinephrine receptor (NER), and of the biogenic amine transporters for serotonin (5-HT), dopamine (DA) and norepinephrine (NE).

The compounds of the invention may also be useful as diagnostic tools or monitoring agents in various diagnostic methods, and in particular for in vivo receptor imaging (neuroimaging), and they may be used in labeled or unlabelled form.

In its first aspect the invention provides azabicyclic aryl derivatives of Formula I

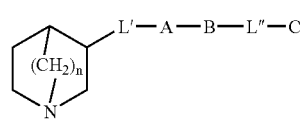

any of its enantiomers or any mixture of its enantiomers, or a prodrug, or a pharmaceutically-acceptable addition salt thereof, wherein n is 1, 2 or 3; and L' represents a linking group selected from —O—, —S—, —CO—, —NR'—, —NR'CO— and —CONR'—; wherein R' represents hydrogen or alkyl; or L' represents the linking group —NY'—; wherein Y' represents formyl, acetyl, propionyl or butanoyl; and A represents an aromatic mono- or bi-cyclic carbocyclic or heterocyclic group, optionally substituted one or more times with substitutents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, alkyl-carbamoyl, amido, N-alkyl-amido, N,N-dialkyl-amido, sulfamoyl, phenyl or benzyl; and B represents a covalent bond (i.e. B is absent); or B represents an aromatic monocyclic carbocyclic or heterocyclic group, optionally substituted one or more times with substitutents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, carboxy, carbamoyl, amido, sulfamoyl and phenyl; and L" represents a linking group selected from —CO—, —CR"=CR'"—, —C≡C—, —NR"—CO—, —CO—NR'"—, —SO$_2$—NR"—, —NR"—SO$_2$—, —NR"—CO—NR'"—; wherein R" and R'", independently of one another, represent hydrogen or alkyl; and C represents an aromatic monocyclic and/or polycyclic, carbocyclic and/or heterocyclic group, optionally substituted one or more times with substitutents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, —NH—CO-alkyl, —NH—CO-cycloalkyl, NH—CO-alkenyl, carboxy, carbamoyl, amido, sulfamoyl, phenyl and —NR""—CO—NHR""', wherein R"" and R""' independently of one another, represent hydrogen or alkyl; or L" represents the linking group —NR"—CO—NY"—; wherein R" represents hydrogen or alkyl; and Y" represents hydrogen, alkyl, aryl-alkyl or heteroaryl-alkyl; and C represents hydrogen, alkyl, aryl-alkyl or heteroaryl-alkyl.

In a second aspect the invention provides pharmaceutical compositions comprising a therapeutically effective amount of the azabicyclic aryl derivative of the invention, or a pharmaceutically-acceptable addition salt thereof, together with at least one pharmaceutically-acceptable carrier or diluent.

Viewed from another aspect the invention relates to the use of the azabicyclic aryl derivative of the invention, or a pharmaceutically-acceptable addition salt thereof, for the manufacture of pharmaceutical compositions/medicaments for the treatment, prevention or alleviation of a disease or a disorder or a condition of a mammal, including a human, which disease, disorder or condition is responsive to modulation of cholinergic receptors.

In yet another aspect the invention provides a method for treatment, prevention or alleviation of diseases, disorders or conditions of a living animal body, including a human, which disorder, disease or condition is responsive to modulation of cholinergic receptors, and which method comprises the step of administering to such a living animal body in need thereof a therapeutically effective amount of the azabicyclic aryl derivative of the invention.

Other objects of the invention will be apparent to the person skilled in the art from the following detailed description and examples.

DETAILED DISCLOSURE OF THE INVENTION

Azabicyclic Aryl Derivatives

In a first aspect the invention provides an azabicyclic aryl derivative of Formula I

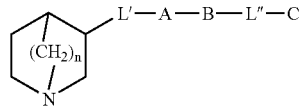

any of its enantiomers or any mixture of its enantiomers, or a prodrug, or a pharmaceutically-acceptable addition salt thereof, wherein n is 1, 2 or 3; and L' represents a linking group selected from —O—, —S—, —CO—, —NR'—, —NR'CO— and —CONR'—; wherein R' represents hydrogen or alkyl; or L' represents the linking group —NY'—; wherein Y' represents formyl, acetyl, propionyl or butanoyl; and A represents an aromatic mono- or bi-cyclic carbocyclic or heterocyclic group, optionally substituted one or more times with substitutents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, alkyl-carbamoyl, amido, N-alkyl-amido, N,N-dialkyl-amido, sulfamoyl, phenyl or benzyl; and B represents a covalent bond (i.e. B is absent); or B represents an aromatic monocyclic carbocyclic or heterocyclic group, optionally substituted one or more times with substitutents selected from the group consisting of alkyl, cycloalkyl, cycloalkyl-alkyl, hydroxy, alkoxy, hydroxy-alkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, carboxy, carbamoyl, amido, sulfamoyl and phenyl; and L" represents a linking group selected from —CO—, —CR"=CR'"—, —C≡C—, —NR"—CO—, —CO—NR"—, —SO$_2$—NR"—, —NR"—SO$_2$—, —NR"—CO—NR'"—; wherein R" and R'", independently of one another, represent hydrogen or alkyl; and C represents an aromatic monocyclic and/or polycyclic, carbocyclic and/or heterocyclic group, optionally substituted one or more times with substitutents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, —NH—CO-alkyl, —NH—CO-cycloalkyl, NH—CO-alkenyl, carboxy, carbamoyl, amido, sulfamoyl, phenyl and —NR""—CO—NHR'"", wherein R"" and R'"", independently of one another, represent hydrogen or alkyl; or L" represents the linking group —NR"—CO—NY"—; wherein R" represents hydrogen or alkyl; and Y" represents hydrogen, alkyl, aryl-alkyl or heteroaryl-alkyl; and C represents hydrogen, alkyl, aryl-alkyl or heteroaryl-alkyl.

In a preferred embodiment the azabicyclic aryl derivative of the invention is a compound of Formula I, wherein n is 1, 2 or 3.

In a more preferred embodiment n is 1 or 2.

In another preferred embodiment the azabicyclic aryl derivative of the invention is a compound of Formula I, wherein L' represents a linking group selected from —O—, —S—, —CO—, —NR'—, —NR'CO— and —CONR'—; wherein R' represents hydrogen or alkyl; or wherein L' represents the linking group —NY'—; wherein Y' represents formyl, acetyl, propionyl or butanoyl.

In a more preferred embodiment L' represents a linking group selected from —O—, —NR'CO— and —CONR'—; wherein R' represents hydrogen or alkyl.

In a third preferred embodiment the azabicyclic aryl derivative of the invention is a compound of Formula I, wherein A represents an aromatic mono- or bi-cyclic carbocyclic or heterocyclic group, optionally substituted one or more times with substitutents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, alkyl-carbamoyl, amido, N-alkyl-amido, N,N-dialkyl-amido, sulfamoyl, phenyl or benzyl; and In a more preferred embodiment A represents an aromatic 5- to 6-membered monocyclic heterocyclic group, optionally substituted one or more times with substitutents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, oxo, carboxy, carbamoyl, alkyl-carbamoyl, amido, N-alkyl-amido, N,N-dialkyl-amido, sulfamoyl, phenyl or benzyl.

In an even more preferred embodiment A represents an aromatic 5-membered monocyclic heterocyclic group.

In a yet more preferred embodiment A represents furanyl, thienyl, pyrrolyl, oxazolyl or imidazolyl.

In a still yet more preferred embodiment A represents furanyl, in particular furan-2,5-diyl, or thienyl, in particular thien-2,5-diyl.

In a fourth preferred embodiment the azabicyclic aryl derivative of the invention is a compound of Formula I, wherein B represents a covalent bond (i.e. B is absent).

In a fifth preferred embodiment the azabicyclic aryl derivative of the invention is a compound of Formula I, wherein B represents an aromatic monocyclic carbocyclic or heterocyclic group, optionally substituted one or more times with substitutents selected from the group consisting of alkyl, cycloalkyl, cycloalkyl-alkyl, hydroxy, alkoxy, hydroxy-alkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, carboxy, carbamoyl, amido, sulfamoyl and phenyl.

In a more preferred embodiment B represents an aromatic monocyclic carbocyclic group, optionally substituted one or more times with substitutents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, carboxy, carbamoyl, amido, sulfamoyl and phenyl.

In an even more preferred embodiment B represents an aromatic monocyclic carbocyclic group.

In a yet more preferred embodiment B represents a phenyl group.

In a sixth preferred embodiment the azabicyclic aryl derivative of the invention is a compound of Formula I, wherein L" represents a linking group selected from —CO—, —CR"=CR'"—, —C≡C—, —NR"—CO—, —CO—NR"—, —SO$_2$—NR"—, —NR"—SO$_2$—, —NR"—CO—NR'"—; wherein R" and R'", independently of one another, represent hydrogen or alkyl.

In a more preferred embodiment L" represents a linking group selected from —CO—, —C≡C—, —NR"—CO—, —CO—NR"- and —NR"—CO—NR'"—; wherein R" and R'", independently of one another, represent hydrogen or alkyl.

In an even more preferred embodiment L" represents —CO—, —C≡C—, —NH—CO— or —NH—CO—NH—.

In a seventh preferred embodiment the azabicyclic aryl derivative of the invention is a compound of Formula I, wherein C represents an aromatic monocyclic and/or polycyclic, carbocyclic and/or heterocyclic group, optionally substituted one or more times with substitutents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, —NH—CO-alkyl, —NH—CO-cycloalkyl, NH—CO-alkenyl, carboxy, carbamoyl, amido, sulfamoyl, phenyl and —NR""—CO—NHR"""—, wherein R"" and R""", independently of one another, represent hydrogen or alkyl.

In a more preferred embodiment C represents an aromatic monocyclic and/or polycyclic, carbocyclic and/or heterocyclic group, optionally substituted one or more times with substitutents selected from the group consisting of alkyl, cycloalkyl, cycloalkyl-alkyl, hydroxy, alkoxy, hydroxyalkoxy, alkoxy-alkyl, alkoxy-alkoxy, cycloalkoxy, cycloalkoxy-alkyl, cycloalkoxy-alkoxy, halo, trihaloalkyl, trihaloalkoxy, cyano, nitro, amino, —NH—CO-alkyl, —NH—CO-cycloalkyl, NH—CO-alkenyl, carboxy, carbamoyl, amido, sulfamoyl, phenyl and —NR""—CO—NHR""", wherein R"" and R""", independently of one another, represent hydrogen, alkyl, phenyl or benzyl.

In an even more preferred embodiment C represents an aromatic monocyclic carbocyclic group, optionally substituted one or two times with substitutents selected from halo, trihaloalkyl, trihaloalkoxy, cyano, nitro, amino, —NH—CO-alkyl, —NH—CO-cycloalkyl, NH—CO-alkenyl and —NR""—CO—NHR""", wherein R"" and R""", independently of one another, represent hydrogen or alkyl.

In a yet more preferred embodiment C represents an aromatic monocyclic carbocyclic group, optionally substituted one or two times with substitutents selected from halo, trihaloalkyl, trihaloalkoxy, cyano, nitro, amino, —NH—CO-alkyl, —NH—CO-cycloalkyl, NH—CO-alkenyl and —NR""—CO—NHR""", wherein R"" and R""", independently of one another, represent hydrogen or alkyl.

In an eight preferred embodiment the azabicyclic aryl derivative of the invention is a compound of Formula I, wherein L" represents the linking group —NR"—CO—NY"—; wherein R" represents hydrogen or alkyl; and Y" represents hydrogen, alkyl, aryl-alkyl or heteroaryl-alkyl; and C represents hydrogen, alkyl, aryl-alkyl or heteroaryl-alkyl.

In a more preferred embodiment

L" represents the linking group —NR"—CO—NY"—; wherein R" represents hydrogen or alkyl; and Y" represents hydrogen, alkyl or benzyl; and C represents hydrogen, alkyl or benzyl.

In an even more preferred embodiment

L" represents the linking group —NH—CO—NH—; and

C represents hydrogen, alkyl or benzyl.

In a yet more preferred embodiment

L" represents the linking group —NH—CO—NH—; and

C represents hydrogen or alkyl.

In a most preferred embodiment the azabicyclic aryl derivative of the invention is 5-(4-Ureido-phenyl)-furan-2-carboxylic acid (1-aza-bicyclo[2.2.2]oct-3-yl)-amide;

or an enantiomer or a mixture of its enantiomers, or a pharmaceutically-acceptable addition salt thereof.

In a ninth preferred embodiment the azabicyclic aryl derivative of the invention is a compound of Formula I, wherein n is 2;

L' represents —NH—CO— or —N(alkyl)-CO—;

A represents furan-2,5-diyl;

B represents phenyl;

L" represents —NH—CO— or —NR"—CO—NR'"—; wherein

R" and R'", independently of one another, represent hydrogen or alkyl; and

C represents phenyl, optionally substituted once or twice with substitutents selected from halo, trihaloalkyl, trihaloalkoxy, cyano, nitro, amino, —NH—CO-alkyl, —NH—CO-cycloalkyl, NH—CO-alkenyl, —NH—CO—NH$_2$ and —NH—CO—NH-alkyl.

In a tenth preferred embodiment the azabicyclic aryl derivative of the invention is a compound of Formula I, wherein n is 2;

L' represents —NH—CO— or —N(alkyl)-CO—;

A represents furan-2,5-diyl;

B represents phenyl;

L" represents —NH—CO—; and

C represents an aromatic monocyclic carbocyclic group, optionally substituted once or twice with substitutents selected from halo, trihaloalkyl, trihaloalkoxy, cyano, nitro, —NH—CO—NH$_2$ and —NH—CO—NH-alkyl.

In an eleventh preferred embodiment the azabicyclic aryl derivative of the invention is a compound of Formula I, wherein n is 2;

L' represents —NH—CO— or —N(alkyl)-CO—;

A represents furan-2,5-diyl;

B represents phenyl;

L" represents —NH—CO— or —NH—CO—NH—; and

C represents phenyl, optionally substituted once or twice with substitutents selected from halo, trifluoromethyl, trifluoromethoxy, cyano, nitro, amino, acetylamino, cyclopropanecarbonyl-amino, acryloylamino, ureido and N-alkyl-ureido.

In a most preferred embodiment the azabicyclic aryl derivative of the invention is (±)5-(4-Benzoylamino-phenyl)-furan-2-carboxylic acid(1-aza-bicyclo[2.2.2]oct-3-yl)-amide;

(±)5-[4-(4-Nitro-benzoylamino)-phenyl]-furan-2-carboxy-
   lic acid(1-aza-bicyclo[2.2.2]oct-3-yl)-amide;
(±)5-[4-(4-Amino-benzoylamino)-phenyl]-furan-2-car-
   boxylic acid(1-aza-bicyclo[2.2.2]oct-3-yl)-amide;
(±)5-[4-(4-Acetylamino-benzoylamino)-phenyl]-furan-2-
   carboxylic acid(1-aza-bicyclo[2.2.2]oct-3-yl)-amide;
(±)5-[4-(4-Acryloylamino-benzoylamino)-phenyl]-furan-2-
   carboxylic acid(1-aza-bicyclo[2.2.2]oct-3-yl)-amide;
(±)5-{4-[4-(Cyclopropanecarbonyl-amino)-benzoylamino]-
   phenyl}-furan-2-carboxylic acid(1-aza-bicyclo[2.2.2]oct-
   3-yl)-amide;
(±)5-[4-(3-Ethyl-ureido)-phenyl]-furan-2-carboxylic acid(1-
   aza-bicyclo[2.2.2]oct-3-yl)-amide;
(±)5-[4-(3-Phenyl-ureido)-phenyl]-furan-2-carboxylic acid
   (1-aza-bicyclo[2.2.2]oct-3-yl)-amide;
(±)5-{4-[3-(4-Nitro-phenyl)-ureido]-phenyl}-furan-2-car-
   boxylic acid(1-aza-bicyclo[2.2.2]oct-3-yl)-amide;
(±)5-{4-[3-(4-Amino-phenyl)-ureido]-phenyl}-furan-2-car-
   boxylic acid(1-aza-bicyclo[2.2.2]oct-3-yl)-amide; or
(±)5-{4-[3-(4-Acetylamino-phenyl)-ureido]-phenyl}-furan-
   2-carboxylic acid (1-aza-bicyclo[2.2.2]oct-3-yl)-amide;
or an enantiomer or a mixture of its enantiomers, or a
pharmaceutically-acceptable addition salt thereof.

Any combination of two or more of the embodiments described herein is considered within the scope of the present invention.

Definition of Substituents

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention a cycloalkoxy group designates a "cycloalkyl-O—" group, wherein cycloalkyl is as defined above.

In the context of this invention a cyano-alkyl group designates an alkyl group substituted with CN, wherein alkyl is as defined above.

In the context of this invention halo represents fluoro, chloro, bromo or iodo, and haloalkyl and haloalkoxy groups designate alkyl and alkoxy groups as defined herein, which alkyl or alkoxy group is substituted one or more times with halo. Thus a trihalomethyl group represents e.g. a trifluoromethyl group, a trichloromethyl group, and similar trihalosubstituted alkyl groups, and a trihaloalkoxy group designates e.g. a trifluoromethoxy group, a trichlormethoxy, and similar trihalosubstituted alkoxy groups. Preferred haloalkyl groups of the invention include trihalogenmethyl, preferably $CF_3$, and preferred trihaloalkoxy groups of the invention include trihalomethoxy, preferably $CF_3O$.

In the context of this invention an aryl group designates a monocyclic or polycyclic aromatic hydrocarbon group. Examples of preferred aryl groups of the invention include phenyl, indenyl, naphthyl, azulenyl, fluorenyl, and anthracenyl. The most preferred aryl group of the invention is phenyl.

In the context of this invention an aryloxy group designates an "aryl-O—" group, wherein aryl is as defined above. The most preferred aryloxy group of the invention is phenoxy.

In the context of this invention a heteroaryl group designates an aromatic mono- or polycyclic heterocyclic group, which holds one or more heteroatoms in its ring structure. Preferred heteroatoms include nitrogen (N), oxygen (O) and sulphur (S).

Preferred 5-6 membered heteroaryl groups of the invention include furanyl, in particular furan-2- or 3-yl; thienyl, in particular thien-2- or 3-yl; selenophenyl, in particular selenophen-2- or 3-yl; pyrrolyl (azolyl), in particular pyrrol-2- or 3-yl; oxazolyl, in particular oxazol-2,4- or 5-yl; thiazolyl, in particular thiazol-2,4- or 5-yl; imidazolyl, in particular imidazol-2- or 4-yl; pyrazolyl, in particular pyrazol-3- or 4-yl; isoxazolyl, in particular isoxazol-3,4- or 5-yl; isothiazolyl, in particular isothiazol-3-, 4- or 5-yl; oxadiazolyl, in particular 1,2,3-oxadiazol-4- or 5-yl, or 1,3,4-oxadiazol-2-yl; triazolyl, in particular 1,2,3-triazol-4-yl or 1,2,4-triazol-3-yl; thiadiazolyl, in particular 1,2,3-thiadiazol-4- or 5-yl, or 1,3,4-thiadiazol-2-yl; pyridyl, in particular pyrid-2-, 3- or 4-yl; pyridazinyl, in particular pyridazin-3- or 4-yl; pyrimidinyl, in particular pyrimidin-2-, 4- or 5-yl; pyrazinyl, in particular pyrazin-2- or 3-yl; and triazinyl, in particular 1,2,4- or 1,3,5-triazinyl.

More preferred 5 membered heteroaryl groups of the invention include furanyl, in particular furan-2- or 3-yl; thienyl, in particular thien-2- or 3-yl; pyrrolyl (azolyl), in particular pyrrol-2- or 3-yl; oxazolyl, in particular oxazol-2,4- or 5-yl; thiazolyl, in particular thiazol-2,4- or 5-yl; isoxazolyl, in particular isoxazol-3,4- or 5-yl; isothiazolyl, in particular isothiazol-3-, 4- or 5-yl; and thiadiazolyl, in particular 1,2,3-thiadiazol-4- or 5-yl, or 1,3,4-thiadiazol-2-yl.

Most preferred 5 membered heteroaryl groups of the invention include furanyl, in particular furan-2- or 3-yl; and thienyl, in particular thien-2- or 3-yl.

More preferred 6 membered heteroaryl groups of the invention include pyridyl, in particular pyrid-2-, 3- or 4-yl; and pyrazinyl, in particular pyrazin-2- or 3-yl.

In the context of this invention an aromatic bicyclic heterocyclic group designates a bicyclic heterocyclic group, which holds one or more heteroatoms in its ring structure. In the context of this invention the term "bicyclic heterocyclic group" includes benzo-fused five- and six-membered heterocyclic rings containing one or more heteroatoms. Preferred heteroatoms include nitrogen (N), oxygen (O) and sulphur (S).

Preferred bicyclic heteroaryl groups of the invention include indolizinyl, in particular indolizin-2-, 5- or 6-yl; indolyl, in particular indol-2-, 5- or 6-yl; isoindolyl, in particular isoindol-2-, 5- or 6-yl; benzo[b]furanyl, in particular benzofuran-2-, 5- or 6-yl; benzo[b]thienyl, in particular benzothien-2-, 5- or 6-yl; benzoimidazolyl, in particular benzoimidazol-2-, 5- or 6-yl; benzothiazolyl, in particular benzothiazol-5- or 6-yl; purinyl, in particular purin-2- or 8-yl; quinolinyl, in particular quinolin-2-, 3-, 6- or 7-yl; isoquinolinyl, in particular isoquinolin-3-, 6- or 7-yl; cinnolinyl, in particular cinnolin-6- or 7-yl; phthalazinyl, in particular phthalazin-6- or 7-yl; quinazolinyl, in particular quinazolin-2-, 6- or 7-yl; quinoxalinyl, in particular quinoxalin-2- or 6-yl; 1,8-naphthyridinyl, in particular 1,8-naphthyridin-2-, 3-, 6- or 7-yl; and pteridinyl, in particular pteridin-2-, 6- or 7-yl.

More preferred bicyclic heteroaryl groups of the invention include indolyl, in particular indol-2-, 5- or 6-yl; benzo[b]furanyl, in particular benzofuran-2-, 5- or 6-yl; benzo[b]thienyl, in particular benzothien-2-, 5- or 6-yl; benzoimidazolyl, in particular benzoimidazol-2-, 5- or 6-yl; and quinoxalinyl, in particular quinoxalin-2- or 6-yl.

Most preferred bicyclic heteroaryl groups of the invention include indolyl, in particular indol-2-, 5- or 6-yl; benzo[b]furanyl, in particular benzofuran-2-, 5- or 6-yl; benzo[b]thienyl, in particular benzothien-2-, 5- or 6-yl.

In the context of this invention a heteroaryloxy group designates a "heteroaryl-O—" group, wherein heteroaryl is as defined above.

Pharmaceutically Acceptable Salts

The azabicyclic aryl derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzene-sulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts and the cycloalkylalkyl-onium salts.

Particularly preferred onium salts of the invention include those created at the N' position according to the following Formula I'

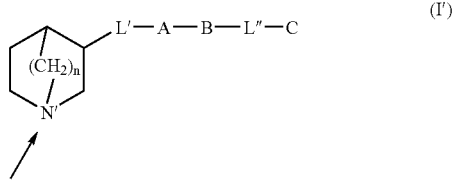

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Producing Azabicyclic Aryl Derivatives

The azabicyclic aryl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The compounds of the present invention are found to be modulators of the nicotinic and/or of the monoamine receptors. Preferred compounds of the invention show a pronounced nicotinic acetylcholine α7 receptor subtype selectivity. The compounds of the present invention may in particular be agonists, partial agonists, antagonists and/or allosteric modulators of the nicotinic acetylcholine receptor.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labeled or unlabelled form.

In a preferred embodiment the compounds of the invention are used for the treatment of diseases, disorders, or conditions relating to the central nervous system. Such diseases or disorders includes anxiety, cognitive disorders, learning deficit, memory deficits and dysfunction, Alzheimer's disease, attention deficit, attention deficit hyperactivity disorder (ADHD), Parkinson's disease, Huntington's disease, Amyotrophic Lateral Sclerosis, Gilles de la Tourette's syndrome, psychosis, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a preferred embodiment diseases, disorders, or conditions relating to the central nervous system for which the compounds of the invention are used are cognitive disorders, psychosis, schizophrenia and/or depression.

In another preferred embodiment the compounds of the invention may be useful for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation and erectile difficulty.

In yet another preferred embodiment the compounds of the invention may be useful for the treatment of endocrine disorders, such as thyrotoxicosis, pheochromocytoma, hypertension and arrhythmias.

In still another preferred embodiment the compounds of the invention may be useful for the treatment of neurodegenerative disorders, including transient anoxia and induced neuro-degeneration.

In even another preferred embodiment the compounds of the invention may be useful for the treatment of inflammatory diseases, disorders, or conditions, including inflammatory skin disorders such as acne and rosacea, Chron's disease, inflammatory bowel disease, ulcerative colitis and diarrhoea.

In still another preferred embodiment the compounds of the invention may be useful for the treatment of mild, moderate or even severe pain of acute, chronic or recurrent character, as well as pain caused by migraine, postoperative pain and phantom limb pain. The pain may in particular be neuropathic pain, chronic headache, central pain, pain related to diabetic neuropathy, to post therapeutic neuralgia, or to peripheral nerve injury.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Pharmaceutical Compositions

In another aspect the invention provides novel pharmaceutical compositions comprising a therapeutically effective amount of an azabicyclic aryl derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents and/or other customary pharmaceutical auxiliaries.

In a preferred embodiment, the invention provides pharmaceutical compositions comprising the azabicyclic aryl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The azabicyclic aryl derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors, and which method comprises administering to such a living animal body, including a human, in need thereof an effective amount of an azabicyclic aryl derivative of the invention.

In the context of this invention the term "treatment" covers treatment, prevention, prophylaxis or alleviation, and the term "disease" covers illnesses, diseases, disorders and conditions related to the disease in question.

The preferred indications contemplated according to the invention are those stated above.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents.

5-(4-Nitrophenyl)-2-furoyl chloride

Was prepared by stirring a mixture of 5-(4-nitrophenyl)-2-furoic acid (1.0 g, 4.3 mmol) and thionyl chloride (10 ml) at reflux for 2 hours. The mixture was evaporated and co-evaporated with anhydrous toluene. The acid chloride was used without further purification.

(±)5-(4-Nitro-phenyl)-furan-2-carboxylic acid(1-aza-bicyclo[2.2.2]oct-3-yl)-amide A mixture of (±)3-aminoquinuclidine dihydrochloride, methanol (250 ml), sodium methoxide (5.1 g, 95 mmol) was stirred at reflux for 1 hour. The mixture was evaporated and was mixed with methanol (150 ml) and dichloromethane (100 ml) was added and cooled on ice, and 5-(4-nitrophenyl)-2-furoyl chloride (11.2 g, 44.5 mmol), solved in dichloromethane (200 ml) was added drop-wise at 0° C. The mixture was stirred at room temperature for 21 hours. The mixture was evaporated, water (200 ml) was added and the pH was adjusted to 8.5 with triethylamine. The mixture was extracted with ethyl acetate (3×200 ml) and the pure product was isolated as free base. Yield 5.0 g (33%).

(±)5-(4-Amino-phenyl)-furan-2-carboxylic acid(1-aza-bicyclo[2.2.2]oct-3-yl)-amide free base A mixture of 5-(4-nitro-phenyl)-furan-2-carboxylic acid (1-aza-bicyclo[2.2.2]oct-3-yl)-amide (5.0 g, 14.6 mmol), palladium on carbon (0.5 g, 10%) and ethanol (250 ml) was stirred under hydrogen atmosphere for 2 hours. The palladium was filtered off on celite. The crude mixture was purified by silica gel chromatography, using a mixture of dichloromethane:methanol (9:1) and 1% methanol as eluent. Yield 2.5 g (55%). M.p. 103-113° C.

(±)5-(4-Benzoylamino-phenyl)-furan-2-carboxylic acid(1-aza-bicyclo[2.2.2]oct-3-yl)-amide hydrochloric acid salt (Compound 1)

A mixture of 5-(4-amino-phenyl)-furan-2-carboxylic acid (1-aza-bicyclo[2.2.2]oct-3-yl)-amide (0.155 g, 0.5 mmol), dichloromethane (25 ml) and benzoyl chloride (0.117 ml, 1.0 mmol) was stirred for 3 hours at room temperature. The crude mixture was filtered. The product was precipitated from the filtrate by adding diethyl ether (5 ml) as hydrochloric acid salt. Yield 56 mg (25%). M.p. 215° C.

In analogy herewith the following compounds are prepared:

(±)5-[4-(4-Nitro-benzoylamino)-phenyl]-furan-2-carboxylic acid(1-aza-bicyclo[2.2.2]oct-3-yl)-amide;

(±)5-[4-(4-Amino-benzoylamino)-phenyl]-furan-2-carboxylic acid(1-aza-bicyclo[2.2.2]oct-3-yl)-amide;

(±)5-[4-(4-Acetylamino-benzoylamino)-phenyl]-furan-2-carboxylic acid(1-aza-bicyclo[2.2.2]oct-3-yl)-amide;

(±)5-[4-(4-Acryloylamino-benzoylamino)-phenyl]-furan-2-carboxylic acid(1-aza-bicyclo[2.2.2]oct-3-yl)-amide;

(±)5-{4-[4-(Cyclopropanecarbonyl-amino)-benzoylamino]-phenyl}-furan-2-carboxylic acid(1-aza-bicyclo[2.2.2]oct-3-yl)-amide;

(±)5-[4-(3-Ethyl-ureido)-phenyl]-furan-2-carboxylic acid(1-aza-bicyclo[2.2.2]oct-3-yl)-amide;

(±)5-[4-(3-Phenyl-ureido)-phenyl]-furan-2-carboxylic acid (1-aza-bicyclo[2.2.2]oct-3-yl)-amide;

(±)5-{4-[3-(4-Nitro-phenyl)-ureido]-phenyl}-furan-2-carboxylic acid(1-aza-bicyclo[2.2.2]oct-3-yl)-amide;

(±)5-{4-[3-(4-Amino-phenyl)-ureido]-phenyl}-furan-2-carboxylic acid(1-aza-bicyclo[2.2.2]oct-3-yl)-amide; and (±)5-{4-[3-(4-Acetylamino-phenyl)-ureido]-phenyl}-furan-2-carboxylic acid (1-aza-bicyclo[2.2.2]oct-3-yl)-amide.

Example 2

In vitro Inhibition of $^3$H-α-Bungarotoxine Binding in Rat Brain

In this example the affinity of the compounds of the invention for binding to $α_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist. $^3$H-α-Bungarotoxine labels nicotinic acetylcholine receptors formed by the $α_γ$ subunit isoform found in brain and the $α_1$ isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM MgSO$_4$ and 2.5 mM CaCl$_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 μl of homogenate are added to 25 μl of test solution and 25 μl of $^3$H-α-bungarotoxine (2 nM, final concentration) and mixed and incubated for 2 hours at 37° C.

Non-specific binding is determined using (−)-nicotine (1 mM, final concentration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an $IC_{50}$ (the concentration of the test substance which inhibits the specific binding of $^3$H-α-bungarotoxin by 50%).

The results of these experiments are presented in Table 1 below.

TABLE 1

| Inhibition of $^3$H-α-Bungarotoxine Binding | |
|---|---|
| Compound No. | $IC_{50}$ (μM) |
| 1 | 0.080 |

The invention claimed is:

1. An azabicyclic aryl derivative represented by Formula I

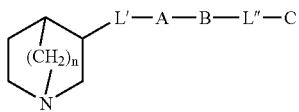

any of its enantiomers or any mixture of its enantiomers, or a pharmaceutically-acceptable addition salt thereof, wherein
n is 2; and
L' represents a linking group selected from —NH—CO— or —N(alkyl)-CO—; and
A represents furan-2,5-diyl; and
B represents phenyl; and
L" represents a linking group selected from —NH—CO— or —NR"—CO—NR'"— wherein R" and R'", independently of one another, represent hydrogen or alkyl; and
C represents phenyl, optionally substituted one or two times with substituents selected from the group consisting of halo, trihaloalkyl, trihaloalkoxy, cyano, nitro, amino, —NH—CO-alkyl, —NH—CO-cycloalkyl, NH—CO-alkenyl, —NH—CO—NH$_2$, and —NH—CO—NH-alkyl.

2. The azabicyclic aryl derivative of claim 1, which is
(±)5-(4-Benzoylamino-phenyl)-furan-2-carboxylic acid (1-aza-bicyclo[2.2.2]oct-3-yl)-amide;
(±)5-[4-(4-Nitro-benzoylamino)-phenyl]-furan-2-carboxylic acid (1-aza-bicyclo[2.2.2]oct-3-yl)-amide;
(±)5-[4-(4-Amino-benzoylamino)-phenyl]-furan-2-carboxylic acid (1-an-bicyclo[2.2.2]oct-3-yl)-amide;
(±)5-[4-(4-Acetylamino-benzoylamino)-phenyl]-furan-2carboxylic acid(1-aza-bicyclo[2.2.2]oct-3-yl)-amide;
(±)5-[4-(4-Acryloylamino-benzoylamino)-phenyl]-furan-2-carboxylic acid(1-aza-bicyclo[2.2.2]oct-3-yl)-amide;
(±)5-{4-[4-(Cyclopropanecarbonyl-amino)-benzoylamino]-phenyl}-furan-2-carboxylic acid(1-aza-bicyclo[2.2.2]oct-3-yl)-amide;
(±)5-[4-(3-Ethyl-ureido)-phenyl]-furan-2-carboxylic acid (1-aza-bicyclo[2.2.2]oct-3-yl)-amide;
(±)5-[4-(3-Phenyl-ureido)-phenyl]-furan-2-carboxylic acid(1-aza-bicyclo[2.2.2]oct-3-yl)-amide;
(±)5-{4-[3-(4-Nitro-phenyl)-ureido]-phenyl}-furan-2-carboxylic acid(1-aza-bicyclo[2.2.2]oct-3-yl)-amide;
(±)5-{4-[3-(4-Amino-phenyl)-ureido]-phenyl}-furan-2-carboxylic acid(1-aza-bicyclo[2.2.2]oct-3-yl)-amide; or
(±)5-{4-[3-(4-Acetylamino-phenyl)-ureido]-phenyl}-furan-2-carboxylic acid(1-aza-bicyclo[2.2.2]oct-3-yl)-amide,
or an enantiomer or a mixture of its enantiomers, or a pharmaceutically-acceptable addition salt thereof.

3. A pharmaceutical composition comprising a therapeutically effective amount of an azabicyclic aryl derivative of claim 1, or a pharmaceutically-acceptable addition salt thereof, together with at least one pharmaceutically-acceptable carrier or diluent.

4. The azabicyclic aryl derivative of claim 1, wherein
n is 2;
L' represents —NH—C— or —N(alkyl)-CO—;
A represents furan-2,5-diyl;
B represents phenyl;
L" represents —NH—CO— or —NH—CO—NH—; and
C represents phenyl, optionally substituted once or twice with substituents selected from halo, trihaloalkyl, trihaloalkoxy, cyano, nitro, amino, acetylamino, cyclopropane-carbonyl-amino, acryloylamino, ureido, and N-alkyl-ureido,
or an enantiomer or a mixture of its enantiomers, or a pharmaceutically-acceptable addition salt thereof.

* * * * *